US010370636B2

(12) United States Patent
Van Hee

(10) Patent No.: US 10,370,636 B2
(45) Date of Patent: Aug. 6, 2019

(54) STARTER CULTURE COMPOSITIONS

(75) Inventor: Pim Van Hee, Delft (NL)

(73) Assignee: DSM IP ASSETS B.V., Heerlen (NL)

( * ) Notice: Subject to any disclaimer, the term of this patent is extended or adjusted under 35 U.S.C. 154(b) by 13 days.

(21) Appl. No.: 13/990,742

(22) PCT Filed: Dec. 8, 2011

(86) PCT No.: PCT/EP2011/072233
§ 371 (c)(1),
(2), (4) Date: Aug. 19, 2013

(87) PCT Pub. No.: WO2012/076665
PCT Pub. Date: Jun. 14, 2012

(65) Prior Publication Data
US 2013/0337108 A1 Dec. 19, 2013

(30) Foreign Application Priority Data

Dec. 10, 2010 (EP) .................................... 10194585
Dec. 10, 2010 (EP) .................................... 10194587

(51) Int. Cl.
*C12N 1/04* (2006.01)
*C12N 1/38* (2006.01)
*A23C 9/123* (2006.01)
(52) U.S. Cl.
CPC ............... *C12N 1/04* (2013.01); *A23C 9/123* (2013.01); *A23C 9/1238* (2013.01); *C12N 1/38* (2013.01)
(58) Field of Classification Search
CPC .... C12N 1/04; C12N 1/20; C12N 1/38; A23C 9/123; A23L 1/0029; A23L 1/0032
USPC ......................................................... 426/38
See application file for complete search history.

(56) References Cited

U.S. PATENT DOCUMENTS

| 4,262,023 | A | 4/1981 | Eddy et al. | |
|---|---|---|---|---|
| 5,952,021 | A | * 9/1999 | Santus | A23C 9/1206 426/34 |
| 2004/0101934 | A1* | 5/2004 | Choe | A23J 1/18 435/91.1 |
| 2004/0247580 | A1* | 12/2004 | Chung et al. | 424/93.45 |
| 2005/0069862 | A1 | 3/2005 | Kringelum et al. | |
| 2006/0204484 | A1 | 9/2006 | Bisgaard-Frantzen et al. | |
| 2007/0010003 | A1 | 1/2007 | Berger et al. | |

FOREIGN PATENT DOCUMENTS

| CN | 101028289 A | 9/2007 |
|---|---|---|
| CN | 101028290 A | 9/2007 |
| CN | 101219152 A | 8/2013 |
| EP | 0259739 A1 | 3/1988 |
| JP | 50071891 A | 6/1975 |
| WO | 9111509 A1 | 8/1991 |
| WO | 0039281 A2 | 7/2000 |
| WO | 2004065584 A1 | 8/2004 |
| WO | 2005003327 A1 | 1/2005 |
| WO | 2005080548 A1 | 9/2005 |
| WO | 2009056979 A1 | 5/2009 |
| WO | 2011/018509 A1 | 2/2011 |

OTHER PUBLICATIONS

Kurultay, et al., "Determination of the Effects of Different Amino Acids, Sodium Formate and Their Combinations on Some Growth Characteristics of Mixed and Single Cell Cultures of Yoghurt Bacteria," Journal of Tekirdag Agricultural Faculty, 2005;2(2):153-160.
International Search Report for PCT/EP2011/072233 dated Mar. 16, 2012.
Ishibashi, Norio et al., "Effect of Water Activity on the Viability of Freeze-Dried Bifidobacteria and Lactic Acid Bacteria and Lactic Acid Bacteria", The British Library—"The world's knowledge", pp. 227-232.
Fraboulet, Pascal, Affidavit dated Aug. 29, 2018.
Vasilean, Ina, Affidavit dated Aug. 9, 2018.
Simitaru, Ina et al., "Researches Concerning the Biosynthesis of Exopolysaccharides in the Fermented Dairy Products with the Yogurt Culture YF-L 811", Bulletin USAMV-CN, 63/2007.
Simitaru, Ina et al., "Sensorial characteristics of yogurt obtained with YF-L811 culture", The Annals of the University of Dunarea de Jos of Galati, Fascicle IV—Food Technology, 2007.
Jorgensen, Leif Friis, Affidavit dated Aug. 28, 2018.
Naturmaelk, Invoices of Chr. Hansen for culture YFL811.
Davanzo, Walter, Affidavit dated Aug. 28, 2018.
"New generation mozzarella cultures offer savings and optimum consistency", CHR Hansen, Press Release, Feb. 17, 2009.
Poulsen, Per, Affidavit dated Aug. 27, 2018.
Jakobsen, Stein Durhuus, Affidavit dated Aug. 29, 2018.
Bisgaard-Frantzen, Hans, Expert Declaration dated Aug. 29, 2018.
Gilliland, S.E. et al., "Frozen Concentrated Cultures of Lactic Starter Bacteria. A Review", J. Milk Food Technol., 1974, vol. 37, No. 2, pp. 107-111.
Broome, M.C. et al., "Starter culture development for improved cheese flavour", Australian Starter Culture Research Centre, Australia, pp. 157-176.
Speckman, C.A. et al., "Lyophilized Lactic Acid Starter Culture Concentrates: Preparation and Use in Inoculation of Vat Milk for Cheddar and Cottage Cheese", Journal of Dairy Science, vol. 57, No. 2, pp. 165-173.
Notice of Opposition to European Patent No. 2649175 dated Sep. 7, 2018.

(Continued)

*Primary Examiner* — Jeffrey P Mornhinweg
(74) *Attorney, Agent, or Firm* — McBee Moore Woodward & Vanik IP, LLC

(57) ABSTRACT

The present invention relates to frozen and freeze dried starter culture compositions comprising microorganisms. The invention also relates to methods of producing the frozen and freeze dried starter culture compositions and methods of using them.

14 Claims, No Drawings

(56) References Cited

OTHER PUBLICATIONS

Notice of Opposition to European Patent No. 2649175 dated Sep. 10, 2018, pp. 1-45.
Notice of Opposition to European Patent No. 2649175 dated Sep. 10, 2018, pp. 1-35.

* cited by examiner

STARTER CULTURE COMPOSITIONS

CROSS REFERENCE TO RELATED APPLICATIONS

This application is a § 371 National Stage Application of PCT/EP2011/072233, filed Dec. 8, 2011, which claims priority to European Application Nos. 10194587.1, filed Dec. 10, 2010; and 10194585.5, filed Dec. 10, 2010.

BACKGROUND OF THE INVENTION

Field of the Invention

The present invention relates to the field of starter culture compositions, in particular frozen and freeze-dried starter culture compositions. Moreover, the invention relates to the production of the frozen and freeze-dried starter culture compositions and their use in manufacturing numerous food and feed products.

Description of Related Art

Lactic acid bacteria are used world-wide in the dairy industry to produce a variety of fermented dairy products such as cheese, yoghurts, sour cream, kefir, butter and koumiss. Selected strains of lactic acid bacteria initiating and carrying out the desired fermentations essential in the manufacture of the above products are often referred to as starter cultures.

Lactic acid bacteria commonly used in the food industry can be divided into mesophilic lactic acid bacteria including the genera *Lactococcus, Leuconostoc* and *Pediococcus* and thermophilic lactic acid bacteria including the genera *Streptococcus* and *Lactobacillus*. While mesophilic lactic acid bacteria have a optimum growth temperature of about 30° C., thermophilic lactic acid bacteria have a optimum growth temperature of about 40° C. to about 45° C.

Starter cultures can be inoculated directly into milk without intermediate transfer and/or propagation. Such starter cultures are generally referred to as direct vat set (DVS) or direct-to-vat inoculation (DVI) cultures.

Starter cultures are generally available from commercial manufacturers in lyophilized/freeze-dried, frozen or liquid form. They can comprise only a single lactic acid bacterium species, but can also be mixed cultures comprising two or more different lactic acid bacterium species.

In order to maintain high cell counts, improved stability and/or viability and/or metabolic activity of lyophilized/freeze-dried, frozen and liquid starter cultures, the addition of additives such as nutrients and cryoprotectants is typically employed.

In EP-0259739-A1 in the name of Miles Laboratories a cryoprotectant together with a combination of citric acid and glucose or a carbohydrate containing glucose linkages are added to culture suspensions before freezing and subsequent freeze-drying of the cultures. The cryoprotectant in EP-0259739-A1 may be sucrose, a peptone, casitone, a salt of glutamic acid, glycerol, dimethyl sulfoxide, non-fat dry milk, casein, whey, fructose or maltose. The combination of citric acid and glucose or the carbohydrate containing glucose linkages acts as a potentiator of the cryoprotectant and further increases the storage stability of the freeze-dried culture concentrate.

WO91/11509 in the name of ICI describes freeze-dried cultures comprising a combination of an ascorbic acid antioxidant and a monocarboxylic α-amino acid which acts as a potentiator for the antioxidant. Said combination is added to the cultures before freezing and subsequent freeze-drying of the cultures. Optionally, a combination of a carbohydrate and a viscosity inducer and a cryoprotectant is added as well. The cryoprotectant may be a glycopeptide and/or the non-toxic, water soluble salt thereof, non-fat skimmed milk powder and/or whey powder, or may be the carbohydrate such as sucrose, mannitol, trehalose, inositol, adonitol and combinations of two or more of these carbohydrates.

WO00/39281 in the name of Chr. Hansen A/S describes a liquid (i.e. a non-frozen) starter culture comprising additives that have a metabolic activity stabilizing effect on the cultures during storage. These liquid starter cultures are presented as a useful alternative to the use of commercial frozen and freeze-dried starter cultures. A suitable additive which, according to WO00/39281, has a metabolic activity stabilizing effect on the cultures during storage is a compound selected from the group consisting of formic acid, a formate, inosinate (IMP), serine and a compound involved in the biosynthesis of nucleic acids, including adenosine-5'-monophosphate (AMP), guanosine-5'-monophosphate (GMP), uranosine-5'-monophosphate (UMP), cytidine-5'-monophosphate (CMP), adenine, guanine, uracil, cytosine, adenosine, guanosine, uridine, cytidine, hypoxanthine, xanthine, hypoxanthine, orotidine, thymidine, inosine and a derivative of any of such compounds.

WO2004/065584 in the name of Chr. Hansen A/S discloses frozen lactic acid bacteria comprising a cryoprotectant agent. The cryoprotectant is added to the bacteria prior to the freezing the bacteria resulting in a homogenous mixture of bacteria and cryoprotectant. The term "a cryoprotective agent" is defined in WO2004/065584 as a substance that is able to improve the storage stability of the frozen culture. The cryoprotective agent in WO2004/065584 may be selected from proteins, protein hydrolysates and amino acids. Preferred suitable examples of these include the ones selected from the group consisting of glutamic acid, lysine, Na-glutamate, Na-caseinate, malt extract, skimmed milk powder, whey powder, yeast extract, gluten, collagen, gelatin, elastin, keratin and albumins. Alternatively the cryoprotective agent may be a carbohydrate. Preferred suitable examples of these include the ones selected from the group consisting pentoses (eg. ribose, xylose), hexoses (eg. fructose, mannose, sorbose), disaccharides (eg. sucrose, trehalose, melibiose, lactulose), oligosaccharides (e.g. raffinose), oligofructoses (e.g. Actilight, fribroloses), polysaccharides (e.g. maltodextrins, xanthan gum, pectin, alginate, microcrystalline cellulose, dextran, PEG), and sugar alcohols (such as sorbitol, mannitol). Also mixtures of cryoprotectants have been disclosed.

WO2005/003327 in the name of Chr. Hansen A/S discloses frozen or freeze-dried cultures comprising one or more cryoprotectants selected from the group consisting of one or more compound(s) involved in the biosynthesis of 5'-nucleic acids or one or more derivative(s) of any such compounds. Inclusion of 3% sodium formate in the frozen lactic acid bacterial culture was found to decrease the storage stability.

WO2005/080548 in the name of Chr. Hansen A/S discloses frozen cultures comprising cryoprotectants. The cryoprotectants are added to the cultures before freezing the cultures.

WO2009/056979 in the name of Danisco discloses frozen starter culture compositions comprising frozen bacteria pellets and separate frozen formate and/or purine pellets and furthermore discloses lyophilized starter culture compositions comprising lyophilized bacteria to which powdered forms of formate and/or purine are added. WO2009/056979 does not disclose the use of a cryoprotectant in the production of the frozen bacterial pellets or the lyophilized bacteria.

In view of the importance of the performance of starter cultures, there is a continuing need in the art to provide starter cultures having improved metabolic activity. The present invention addresses this need.

SUMMARY

In a first aspect the invention relates to a process for making a starter culture composition comprising a microorganism, a cryoprotectant and at least one stimulating additive, the process comprising the steps of
  a) culturing a microorganism in a culture medium; and
  b) collecting the microorganism from the culture medium; and
  c) adding a cryoprotectant to the microorganism obtained in step b); and
  d) freezing the microorganisms obtained in step c); and
  e) adding at least one stimulating additive to the microorganism obtained in step d). In this first embodiment of the process of the invention, the starter culture composition is a frozen starter culture composition.

DETAILED DESCRIPTION OF A PREFERRED EMBODIMENT

In a second embodiment, the microorganisms obtained in step d) are subjected to freeze-drying before adding the at least one stimulating additive to the freeze-dried microorganisms in step e). Freeze-drying is a technique well known in the art and may comprise the steps of freezing microorganisms to get frozen material (step d)) and subsequently reducing the surrounding pressure while adding enough heat to allow the frozen water in the frozen material to sublime directly from the solid phase into the gas phase. Freeze-drying equipment that can be used includes, but is not limited to, rotary evaporator freeze-driers, manifold freeze-driers and tray freeze-driers. If necessary, a secondary step can be performed that aims to remove unfrozen water molecules. It is well within the experience of the person skilled in the art to establish a suitable temperature and pressure profile to achieve satisfactory freeze-drying. The freeze-dried material can be a powder or a granule.

"Starter culture" is defined herein as a preparation containing microbial cells that is intended for inoculating a medium to be fermented. "Microorganism" as used herein includes, but is not limited to, algae, protozoa, viruses, bacteria (such as lactic acid bacteria, *Brevibacterium* and *Propionibacterium*) and fungi (such as the genera *Penicillium, Geotrichum, Saccharomyces* and *Kluyveromyces*). The microorganisms may be non-modified (i.e. wild type) or genetically modified. Genetically modified microorganisms may be provided with and without the use of recombinant DNA-technology.

In a preferred embodiment the microorganism is a fungus or a bacterium. Preferred bacteria are lactic acid bacteria. In the present context, the expression "lactic acid bacteria" designates a group of Gram positive, catalase-negative, non-motile, micro-aerophilic or anaerobic bacteria which ferment sugar with the production of acids. The industrially most useful lactic acid bacteria are found among *Lactococcus* species, *Streptococcus* species, *Enterococcus* species, *Lactobacillus* species, *Leuconostoc* species, *Pediococcus* species and *Bifidobacterium* species. Lactic acid bacteria can be divided into mesophilic and thermophilic lactic acid bacteria. *Lactococcus, Leuconostoc* and *Pediococcus* are examples of genera belonging to the mesophilic lactic acid bacteria. Examples of genera belonging to the thermophilic lactic acid bacteria are *Streptococcus* and *Lactobacillus*.

An example of a *Lactococcus* species is *Lactococcus lactis*. This species can be further subdivided into subspecies including, but not limited to, *Lactococcus lactis cremoris, Lactococcus lactis lactis, Lactococcus lactis lactis* biovar. *diacetylactis* and *Lactococcus lactis hordniae*. Examples of *Leuconostoc* species are *Leuconostoc mesenteroides cremoris* and *Leuconostoc paramesenteroides*. Examples of *Pediococcus* species are *Pediococcus adidilacti* and *Pediococcus pentosaceus*. Examples of *Streptococcus* are *Streptococcus thermophilus* and *Streptococcus salivarius thermophilus*. Examples of *Lactobacillus* species are *Lactobacillus helveticus, Lactobacillus delbruekii* ssp. *bulgaricus, Lactobacillus casei* and *Lactobacillus acidophilus*.

The starter culture may comprise one microorganism or may be a mixed culture comprising two or more different microorganisms. For example, the starter culture may comprise 3 or 4 or 5 or even 6 or more different microorganisms. The starter culture may even comprise probiotics.

In the process of the present invention the microorganisms are produced by culturing microorganisms and isolating the cultured microorganisms. In order to get sufficient amount of microorganisms, it is preferred to make a relatively large-scale fermentation in suitable fermentation tanks, e.g. tanks of at least 50 liters, preferably at least 100 liters.

The microorganism may be cultured as a single microorganism or, in case the starter culture is a mixed starter culture, may be a mixture of microorganisms obtained after cofermentation or coculturing of the different microorganism of the mixed starter culture. Cofermentation and coculturing are synonyms relating to fermentation processes wherein 2 or more microorganisms are cultured as a mixture in one and the same fermentation process. Alternatively, the mixed starter culture may be obtained by mixing the different microorganisms after culturing of the single microorganisms or by mixing a single microorganism with microorganism obtained after a cofermention or coculturing.

In an embodiment the culturing is performed under temperature and/or pH control. The pH control can be internally and/or externally, with external pH control being preferred. Internal pH control includes, but is not limited to, the use of buffering agents. External pH control includes, but is not limited to, addition of aqueous ammonia, sodium hydroxide or other food grade caustic. The pH is controlled at a pH of about 5 or higher, preferably between 5.0 and 7.0. More preferably, the pH is controlled between 5.5 and 6.5 and most preferred between 5.8 and 6.3.

Culturing is carried out at a temperature conducive to the growth of the microorganisms for a period of time until the desired cell concentration and activity of the culture are reached. Culturing can be slowed down by cooling to e.g. below 10° C.

First, microorganisms are introduced into a growth medium and in the incubation step the microorganisms are grown/propagated in the growth medium. In other words, in the introduction step an inoculated medium is produced and in the incubation step the inoculated medium in ripened to produce a culture. The growth medium can be any growth medium suitable for the strains to be propagated. It can be a synthetic growth medium (ready-to-use liquid or powdered medium that first has to be reconstituted), whey or milk.

After fermentation/culturing, the viable cells may be recovered/harvested/isolated/separated from the growth medium by techniques well known to the skilled artisan such as centrifugation, (ultra)filtration or combinations thereof. After isolation, a concentrated culture of microorganisms is obtained. This concentrated culture can be packaged for subsequent use or storage under suitable conditions for a period time. Preferably, the isolated microorganisms have a content of viable cells of at least $1 \times 10^7$ cfu/ml, preferably at least $1 \times 10^8$ cfu/ml, more preferably at least $1 \times 10^9$ cfu/ml, more preferably at least $1 \times 10^{10}$ cfu/ml, most preferably at least $1 \times 10^{11}$ cfu/ml.

Alternatively, the cells can also be aliquoted for subsequent use or storage without previously being recovered/harvested/isolated/separated.

A "cryoprotectant" is defined herein as a substance used to protect cells or tissues from damage during freezing and thawing. The cryoprotectant may be any additive as long as it protects cells or tissues from damage during freezing and thawing.

Examples of cryoprotectants include, but are not limited to, sugars (e.g. sucrose, fructose, trehalose), polyalcohols (e.g. glycerol, sorbitol, mannitol), polysaccharides (e.g. celluloses, starch, gums, maltodextrin), polyethers (e.g. polypropylene glycol, polyethylene glycol, polybutylene glycol), antioxidants (e.g. natural antioxidants such as ascorbic acid, beta-carotene, vitamin E, glutathione, chemical antioxidants), oils (e.g. rapeseed oil, sunflower oil, olive oil), surfactants (e.g. Tween®20, Tween®80, fatty acids), peptones (e.g. soy peptones, wheat peptone, whey peptone), tryptones, vitamins, minerals (e.g. iron, manganese, zinc), hydrolysates (e.g. protein hydrolysates such as whey powder, malt extract, soy), amino acids, peptides, proteins, nucleic acids, nucleotides, nucleobases (e.g. cytosine, guanine, adenine, thymine, uracil, xanthine, hypoxanthine, inosine), yeast extracts (e.g. yeast extracts of *Saccharomyces* spp., *Kluyvermomycesa* spp., or *Torula* spp.), beef extract, growth factors, and lipids. The examples of cryoprotectants include also those cited in the background of the invention The addition of the cryoprotectant in step c) of the process of the invention may be done by mixing solid cryoprotectant with the microorganism obtained in step b) for a suitable amount of time at a suitable temperature. Alternatively, a sterile solution of the additive may be mixed with the biomass. In an embodiment the additive is selected from the group consisting of a cryoprotectant, an excipient, a carrier and a nutrient.

The freezing step d) comprises the step of lowering the temperature of microorganisms obtained in step c) below their freezing point such that there is a phase change in which liquid turns into solid. The frozen material can be made by rapid freezing of the microorganisms. Rapid freezing can be carried out by dripping, injecting, spraying, pouring or dispersing microorganisms as e.g. droplets, particles or a thin stream into a cooling medium at a suitably low temperature. The cooling medium can be a cooled liquid, a cooled solid or a cooled gas, e.g. liquid nitrogen, liquid carbon dioxide or liquid helium. In an embodiment the cooling medium is liquid nitrogen. In another embodiment the cooling medium can be added to the microorganisms by e.g. pouring it into a container of cells or blowing a cooled gas stream over or bubbling a cooled gas stream into a cell suspension. In another embodiment the cells are placed in a container and the container is contacted with a cooling medium. The frozen material can have the form of pellets or granules.

A "stimulating additive" is defined herein as an additive that increases the acidification activity of a microorganism in a precursor material, e.g. a dairy substrate such as for instance milk. In other words, the acidification activity of the microorganisms in the precursor material in the presence of the stimulating additive is higher than the acidification activity of the microorganisms in the precursor material in the absence of the stimulating additive. Acidification activity can be measured by means of the assay as described herein. In one embodiment the stimulating additive is a nutrient. A "nutrient" is defined herein as a compound that can be metabolized by the microorganism and that may stimulate the acidification speed and/or growth of the microorganism in the application. Examples of stimulating additives include, but are not limited to antioxidants (e.g. natural antioxidants such as ascorbic acid, beta-carotene, vitamin E, glutathione, chemical antioxidants), peptones (e.g. soy peptones, wheat peptone, whey peptone), tryptones, vitamins, minerals (e.g. iron, manganese, zinc), hydrolysates (e.g. protein hydrolysates such as whey powder, malt extract, soy), amino acids, peptides, proteins, nucleic acids, nucleotides, nucleobases (e.g. cytosine, guanine, adenine, thymine, uracil, xanthine, hypoxanthine, inosine), yeast extracts (e.g. yeast extracts of *Saccharomyces* spp., *Kluyvermomycesa* spp., or *Torula* spp.), beef extract, organic acids (e.g. formic acid or a salt or ester thereof such as for instance sodium formate, potassium formate, ammonium formate, calcium formate, ethyl formate, methyl formate) and growth factors.

In a preferred embodiment the stimulating additive is a nucleobase such as adenine, a yeast extract, formic acid or a salt or ester thereof such as for instance sodium formate, potassium formate, ammonium formate, calcium formate, ethyl formate, methyl formate. Most preferred are adenine and formic acid or a salt or ester thereof. The stimulating additive can also be a mixture of two or more of the stimulating additives.

In a preferred embodiment the stimulating additive is a solid such as a pellet, granule, a tablet or a powder. For a frozen starter culture composition, the stimulating additive may be added in step e) of the process in a solid form such as a pellet, granule, a tablet or a powder. Most preferably the stimulating additive in a frozen form, preferably as a frozen pellet. The stimulating additive may be added to the frozen microorganism directly after freezing or, alternatively, the frozen bacteria may be stored under suitable conditions for a period of time before the stimulating additive is added to the material.

For a lyophilized starter culture composition, the stimulating additive may be added in a solid form such as a pellet, granule, a tablet or a powder, preferably as a granule or powder, most preferably as a powder.

The frozen starter culture composition comprises preferably from 0.1% to 90%, preferably from 0.5% to 85%, more preferably from 1% to 80%, even more preferably from 2% to 70%, most preferably from 3% to 65%, and in particular from 5% to 60% of the stimulating additive measured as wt/wt of the frozen culture composition. In another embodiment the ratio of stimulating additive to cells, expressed as [weight stimulating additive]/[weight cells] is between 0.01 and 25, preferably between 0.02 and 20, more preferably between 0.05 and 15, even more preferably between 0.07 and 12, and in particular between 0.1 and 10.

The lyophilized starter culture composition comprises preferably from 0.1% to 90%, preferably from 0.5% to 85%, more preferably from 1% to 80%, even more preferably from 2% to 70%, most preferably from 3% to 65%, and in particular from 5% to 60% of a stimulating additive measured as wt/wt of the freeze-dried culture composition. In another embodiment the ratio of stimulating additive to cells, expressed as [weight stimulating additive]/[weight cells] is between 0.01 and 25, preferably between 0.02 and 20, more preferably between 0.05 and 15, even more preferably between 0.07 and 12, and in particular between 0.1 and 10.

In an alternative embodiment the stimulating additive is added to the frozen material and the obtained frozen composition is subjected to sublimation.

In an embodiment the process of the invention further comprises the step of packing the frozen or freeze-dried culture composition. The compositions can be packed in suitable bags (laminate), bottles, containers, cans, boxes or any suitable packaging means. The frozen culture compositions can be stored and transported under refrigeration for extended periods of time. Storage of the frozen culture compositions below −10° C., preferably below −20° C., more preferably below −30° C., even more preferably below −40° C. and in particular below −50° C. is recommended.

The freeze-dried culture compositions can be stored and transported without refrigeration for extended periods of time under dry conditions. However, storage below 0° C. is recommended, more preferably below 15° C.

In a specific embodiment of the process of the present invention to make the freeze-dried starter culture composition, the process comprises a step wherein the freeze-dried microorganism and/or the stimulating additive added to the freeze-dried microorganism and/or the freeze-dried starter culture composition is coated. The coating may comprise well known coating materials such as oil, butter fat, maltodextrin etceteras. The coating may be added to prevent caking of the constituents of the freeze-dried culture compositions according to the present invention and/or to prevent oxidation of the product and/or to prevent moisture uptake.

In a specific embodiment of the process of the present invention another additive selected from the group consisting of an excipient, a carrier and a nutrient is added to the microorganisms before freezing.

In a second aspect, the invention provides a starter culture composition comprising a microorganism, a cryoprotectant and at least one stimulating additive which is preferably obtainable by the process of the invention. The starter culture composition comprising a microorganism, a cryoprotectant and at least one stimulating additive may be a frozen starter culture composition or a freeze-dried starter culture composition. The microorganism, the cryoprotectant and the stimulating additive are identical to those described hereinbefore for the process of the invention (first aspect of the invention).

The obtained frozen and/or freeze-dried culture composition according to the invention typically comprises a content of viable cells of at least $1 \times 10^7$ cfu/g, preferably at least $1 \times 10^8$ cfu/g, more preferably at least $1 \times 10^9$ cfu/g, even more preferably at least $1 \times 10^{10}$ cfu/g, yet even more preferably at least $1 \times 10^{11}$ cfu/g, in particular at least $1 \times 10^{12}$ cfu/g and more in particular at least $1 \times 10^{13}$ cfu/g.

The frozen starter culture composition comprises preferably from 0.1% to 90%, preferably from 0.5% to 85%, more preferably from 1% to 80%, even more preferably from 2% to 70%, most preferably from 3% to 65%, and in particular from 5% to 60% of the stimulating additive measured as wt/wt of the frozen culture composition. In another embodiment the ratio of stimulating additive to cells, expressed as [weight stimulating additive]/[weight cells] is between 0.01 and 25, preferably between 0.02 and 20, more preferably between 0.05 and 15, even more preferably between 0.07 and 12, and in particular between 0.1 and 10.

The lyophilized starter culture composition comprises preferably from 0.1% to 90%, preferably from 0.5% to 85%, more preferably from 1% to 80%, even more preferably from 2% to 70%, most preferably from 3% to 65%, and in particular from 5% to 60% of a stimulating additive measured as wt/wt of the freeze-dried culture composition. In another embodiment the ratio of stimulating additive to cells, expressed as [weight stimulating additive]/[weight cells] is between 0.01 and 25, preferably between 0.02 and 20, more preferably between 0.05 and 15, even more preferably between 0.07 and 12, and in particular between 0.1 and 10.

As indicated above, the freeze-dried culture compositions according to the present invention may be coated.

An aspect of the present invention relates to frozen and/or freeze-dried culture compositions that have a higher metabolic activity, e.g. a higher acidification activity, than frozen and/or freeze-dried culture compositions whereby the stimulating additive is added before freezing. Another aspect of the present invention relates to frozen and/or freeze-dried culture compositions that have an improved shelf life compared to frozen and/or freeze-dried culture compositions whereby the stimulating additive is added before freezing.

Acidification activity can be measured by various assays known to the person skilled in the art. An example of a suitable acidification assay is given in the example section. One example of a suitable medium wherein the acidification activity can be measured is milk and in that case the "acidification activity" as used herein means a change (i.e. decrease) in pH of milk in time when inoculated with a culture composition according to the invention (stimulating additive added after freezing or freeze-drying) and compared to a culture composition having approximately the same cell numbers and stimulating additive concentrations, but wherein stimulating additive is added before freezing the culture.

In a third aspect of the invention the frozen culture composition according to the invention can be present in a package such as a bag. In an embodiment the package may comprise a mixture of frozen culture pellets/granules and stimulating additive pellets/granules or a mixture of frozen culture pellets/granules and stimulating additive powder. Different strains may be present in one package. Different stimulating additives may be present in one package.

In addition, a kit comprising at least a package comprising a frozen culture composition and a package comprising a stimulating additive is a part of the present invention. The package can be a container, a bag, a bottle, box, to name just a few. The same type or a different type of package can be used for the culture and the stimulating additive. The size of the packages can be identical or different. The kit may comprise further packages, if desired. These packages may contain cultures in liquid, freeze-dried or frozen form or further additives in solid or liquid form. As indicated before, the freeze-dried culture composition and/or stimulating additive may be coated. This, among others, to prevent caking.

In a fifth aspect the invention pertains to a process of producing a cultured food or feed product by using a frozen and/or freeze-dried culture composition or a kit according to the invention. So, the invention also relates to a process of making a fermented product, by adding a frozen and/or freeze-dried culture composition or a kit according to the invention to a substrate and allowing it to ferment the substrate to produce a fermented product.

In an embodiment the process of producing a cultured food or feed product or a fermented product comprises the steps of a) inoculating a precursor material with a frozen and/or freeze-dried culture composition or a kit according to the present invention, b) culturing the precursor material with the frozen and/or freeze-dried culture, and c) producing/obtaining the cultured food product. In case a kit is used the packages may be added at the same time to the precursor material or may be added consecutively in any order.

The substrate or precursor material can be a food substrate such as a soya bean substrate, a meat substrate, a substrate for a bakery, wine, beverage, fruit juice or vegetable product or a dairy substrate, e.g. milk. Typically, the fermented product or food product is a dairy food product or dairy food-derived product or fermented milk product, e.g. cheese, yoghurt, butter, quark, sour cream, matured cream, infant milk, cream dessert, ice cream, inoculated sweet milk, buttermilk, kefir, koumiss, milk beverage, fermented whey-based beverage, fermented milk or drinking yoghurt. In another embodiment the fermented product or food product is a meat product, a vegetable product, a beverage product, a wine product, a bakery product, a fruit juice product.

Cheese includes, but is not limited to, soft cheeses, Emmenthal cheeses, cottage cheeses, Feta cheeses, Continental cheeses, Pasta Filata cheeses, Cheddar cheeses, and Grana cheeses.

In another embodiment the frozen and/or freeze-dried culture compositions can be used as probiotics in a probiotically active product such as for example sweet acidophilus milk.

In another embodiment the composition according to the invention can be used to produce a feed product such as silage for example grass or cereal material.

In a sixth aspect, the invention provides the use of a frozen and/or freeze-dried culture composition or kit according to the invention in a process for making a food or feed product is another aspect of the present invention.

Materials and Methods

Acidification Activity Assay of Frozen and Lyophilized Compositions

The acidification activity of the frozen and lyophilized starter culture compositions is determined by inoculating 200 g of 9.5% Reconstituted Skim Milk (RSM) with amounts of the frozen or lyophilized compositions indicated in the Examples. In one experiment, for each composition the same amount of biomass is dosed to the milk. This allows for comparison of the acidification activity at constant lactic acid bacteria concentrations for all compositions of one culture concentrate. In addition, the concentration of the stimulating additive (e.g. sodium formate or yeast extract) is kept the same for comparison of different compositions.

The milk is incubated for at least 6 hours at 31° C. (for e.g. mesophillic lactic acid bacteria) or 37° C. (for e.g. thermophilic lactic acid bacteria). The pH is monitored continuously during the incubation. The time-to-reach (TTR) a pH=5.5 (expressed in minutes) during the incubation is used as a measure for the acidification activity of the compositions. The accuracy and reproducibility of the acidification activity assay are in the order of ±10 minutes.

Freeze Drying

Frozen culture pellets were introduced into a freeze-drying apparatus (VirTis advantage freeze-dryer with Wizard 2.0 data centre (SP Scientific) and vacuum pump (Edwards High Vacuum)) that was pre-conditioned to −25° C. (condenser temperature −68° C.). Then, the temperature and pressure of the apparatus were set to −10° C. and 50 mbar for 40 hours, 25° C. and 50 mbar for 3 hours, and finally to 25° C. and 300 mbar for 25 hours to dry the products.

EXAMPLE 1

Production and Acidification Activity of a Frozen Culture Composition Comprising *Streptococcus Thermophilus*

A *Streptococcus thermophilus* strain is grown in a suitable growth medium. After fermentation, the fermentation broth is centrifuged and a concentrate comprising about $1 \times 10^{11}$ cfu/ml is obtained. The concentrate is divided into two equal batches. To one batch stimulating additive (formate) is added prior to freezing, while to the other batch stimulating additive is added after freezing. In detail, the frozen compositions are prepared as follows.

Composition 1: To one batch of the culture concentrate a 50% (w/w) sodium formate solution is added. The obtained composition comprising 82.3% (w/w) concentrate and 17.7% (w/w) of the 50% (w/w) sodium formate solution is then frozen by dripping it into liquid nitrogen. The obtained frozen products (i.e. frozen culture pellets) are stored at −40° C. until further use. The sodium formate content of composition 1 is 8.875% (w/w) while 82.25% (w/w) is frozen culture concentrate and the remaining 8.875% (w/w) is water from the sodium formate solution.

Composition 2: The other batch of the culture concentrate is frozen by dripping the culture concentrate into liquid nitrogen. To the obtained frozen products (i.e. frozen culture pellets) sodium formate powder is added. The sodium formate content of the composition is 9.73% (w/w); the remaining 90.27% (w/w) is frozen culture concentrate. The obtained composition is stored at −40° C. until further use. This composition is called composition 2. Composition 1 and 2 contain the same ratio of sodium formate and frozen culture concentrate.

Acidification Activity: 16 mg of composition 1 and 14.59 mg of composition 2 were used in the acidification test described in the Materials and Methods section. The results in Table 1 show that composition 2 (sodium formate added after freezing) has a higher acidification activity than composition 1 (sodium formate added to culture concentrate prior to freezing)

EXAMPLE 2

Alternative Production and Acidification Activity of a Frozen Culture Composition Comprising *Streptococcus Thermophilus*

In the production of frozen culture compositions according to Example 1 sodium formate powder is added to the obtained frozen products (i.e. frozen culture pellets). In Example 2 frozen sodium formate pellets are added to the obtained frozen products (i.e. frozen culture pellets). All other steps and conditions are identical to Example 1.

Composition 3: To one batch of the culture concentrate a 50% (w/w) sodium formate solution is added. The obtained composition comprising 82.25% (w/w) concentrate and 17.75% (w/w) of the 50% (w/w) sodium formate solution is then frozen by dripping it into liquid nitrogen. The obtained frozen products (i.e. frozen culture pellets) are stored at −40° C. until further use. The sodium formate content of the composition is 8.875% (w/w) while 82.25% (w/w) is frozen culture concentrate and the remaining 8.875% (w/w) is water from the sodium formate solution. Composition 3 is identical to composition 1.

Composition 4: The other batch of the culture concentrate is frozen by dripping the concentrate into liquid nitrogen. To the obtained frozen products (i.e. frozen culture pellets) frozen sodium formate pellets are added. These pellets contain 40% (w/w) sodium formate, 2% (w/w) Arabic gum and the remainder is water. The frozen sodium formate pellet content of the composition is 21.2% (w/w) while the remaining 78.8% (w/w) is frozen culture concentrate. The obtained composition is stored at −40° C. until further use. Composition 3 and 4 contain the same ratio of sodium formate and frozen culture concentrate.

Acidification activity: 16.7 mg of composition 3 and 18.8 mg of composition 4 were used in the acidification test described in the Materials and Methods section. The results in Table 1 show that composition 4 (sodium formate added after freezing) has a higher acidification activity than composition 3 (sodium formate added to culture concentrate prior to freezing).

TABLE 1

Frozen culture compositions

| Composition | Sodium formate | Cryo-protectant | Acidification rate |
| --- | --- | --- | --- |
| C1 | Added to bacteria suspension prior to freezing | none | C2 > C1 |
| C2 | Formate powder added to frozen culture pellets | | |
| C3 | Added to bacteria suspension prior to freezing | | C4 > C3 |
| C4 | Frozen formate pellets added to frozen culture pellets | | |
| C5 | Added to bacteria suspension prior to freezing | Added to bacteria suspension | C6 > C5 |
| C6 | Formate powder added to frozen culture pellets | | |

EXAMPLE 3

Production and Acidification Activity of Frozen Culture Compositions Comprising *Streptococcus Thermophilus* and a Cryoprotectant Frozen culture compositions 1 and 2 are made as described in Example 1 with the proviso that 10.5 g of a cryoprotectant solution containing (in wt %): maltodextrin (28.6%), sorbitol (10.3%), calcium ascorbate (11.4%), glutamate (2.9%) and water (46.8%) is added to 65.84 g of the culture concentrate directly after centrifugation to give compositions 5 and 6 respectively.

Acidification activity: 18.11 mg of composition 5 and 16.69 mg of composition 6 were used in the acidification test described in the Materials and Methods section. The results in Table 1 show that composition 6 (sodium formate added after freezing) has a higher acidification activity than composition 5 (sodium formate added to culture concentrate prior to freezing).

From Examples 1-3 can be concluded that the separate addition of formate to the frozen culture pellets, either as a powder or as a frozen pellet, results in higher acidification rates compared to adding formate to the bacteria suspension prior to freezing. The addition of a cryoprotectant further enhances the acidification rates of the frozen culture pellets

EXAMPLE 4

Production and Acidification Activity of Freeze-dried Culture Compositions Comprising *Streptococcus Thermophilus*

A *Streptococcus thermophilus* strain was grown as described in Example 1. The concentrate was divided into two equal batches. To one batch stimulating additive was added prior to freezing and drying, while to the other batch stimulating additive was added after freezing and drying. In detail, the freeze-dried compositions were prepared as follows.

Composition 7. To one batch of the culture concentrate a 50% (w/w) sodium formate solution was added. The obtained composition comprising 82.3% (w/w) concentrate and 17.7% (w/w) of the 50% (w/w) sodium formate solution was then frozen by dripping it into liquid nitrogen and subjected to freeze-drying as described under Materials and Methods. The dry matter content after drying was 20.3% relative to the sodium formate containing frozen products that were put into the freeze-drying apparatus. The obtained freeze-dried composition (i.e. a powder composition) was stored at −20° C. until further use. The sodium formate content of the composition was 43.7% (w/w); the remaining 56.3% (w/w) was freeze-dried culture concentrate.

Composition 8. The other batch of the culture concentrate was frozen by dripping the concentrate into liquid nitrogen and subjected to freeze-drying as described under Materials and Methods. To the obtained freeze-dried composition (i.e. a powder composition) sodium formate powder was added. The sodium formate content of the composition was 43.7% (w/w); the remaining 56.3% (w/w) was freeze-dried culture concentrate. The obtained composition was stored at −20° C. until further use. Composition 7 and 8 contained the same ratio of sodium formate and freeze-dried culture concentrate.

Acidification activity: 3.3 mg of composition 7 and composition 8 were used in the acidification test described in the Materials and Methods section. The results in Table 2 show that composition 8 (sodium formate added to the freeze dried culture) has a higher acidification activity than composition 7 (sodium formate added to culture concentrate prior to freezing and drying).

EXAMPLE 5

Production and Acidification Activity of Freeze-dried Culture Compositions Comprising *Streptococcus Thermophilus* and a Cryoprotectant Freeze-dried culture compositions 7 and 8 were made as described in Example 4 with the proviso that 10.5 g of the cryoprotectant solution (see Example 3) was added to 65.84 g of the culture concentrate directly after centrifugation to give compositions 9 and 10 respectively.

Acidification activity: 4.4 mg of composition 9 and composition 10 were used in the acidification test described in the Materials and Methods section. The results in Table 2 show that composition 10 (sodium formate added to the freeze dried culture) has a higher acidification activity than composition 9 (sodium formate added to culture concentrate prior to freezing and drying).

From Examples 4-5 can be concluded that the separate addition of formate to the freeze-dried culture pellets results in higher acidification rates compared to adding formate to the bacteria suspension prior to freezing. The addition of a cryoprotectant further enhances the acidification rates of the freeze-dried culture pellets.

TABLE 2

Freeze-dried culture compositions

| Example | Composition | Bacteria | Sodium formate | Cryoprotectant | TTR pH 5.5 (min) |
|---|---|---|---|---|---|
| 4 | C7 | Lyophilized | Added to bacteria suspension prior to freezing | none | 324 |
|   | C8 |   | Formate powder added to the lyophilized culture |   | 243 |
| 5 | C9 |   | Added to bacteria suspension prior to freezing | Added to bacteria suspension | 248 |
|   | C10 |   | Formate powder added to the lyophilized culture |   | 235 |

EXAMPLE 6

Production and Acidification Activity of Frozen Culture Compositions

Frozen culture compositions were made according to Examples 1-3 with the following variables: as bacterial strains the thermophilic *Streptococcus thermophilus* (same as in Examples 1-5) and *Lactobacillus bulgaricus* and the mesophilic *Lactococcus lactis* were used. As stimulating additive formate or yeast extract abbreviated as YE (Maxarome® batch nr CE/8282 DSG2C35 a high nucleotide product or Gistex® LS Ferm batch nr CE/AFP104) were used. Maxarome® and Gistex® are registered trademarks; the products can be obtained from DSM Food Specialties, Delft, The Netherlands. The cryoprotectant was added as described in Example 3.

The following amounts of the final compositions were dosed into the acidification assay as described in the Material and Methods: 10 mg of compositions C7-C18 and 150 mg of compositions C19-C26.

From Table 3 can be concluded that the separate addition of formate or the yeast extract to the frozen culture pellets results in higher acidification rates compared to adding formate or the yeast extract to the bacteria suspension prior to freezing. The addition of a cryoprotectant further enhances the acidification rates of the frozen culture pellets

EXAMPLE 7

Production and Acidification Activity of Freeze-dried Culture Compositions

Freeze-dried culture compositions were made according to Examples 4-5 with the following variables as described in Example 6. The following amounts of the final compositions were dosed into the acidification assay as described in the Material and Methods: 10 mg of compositions C27-C34 and 50 mg of compositions C35-C38 and 150 mg of compositions C39-C46.

From Table 4 can be concluded that the separate addition of formate or the yeast extract to the freeze-dried culture pellets results in higher acidification rates compared to adding formate or the yeast extract to the bacteria suspension prior to freezing. The addition of a cryoprotectant further enhances the acidification rates of the freeze-dried culture pellets.

TABLE 3

Frozen culture compositions

| Composition | Stimulating additive (SA) | ratio SA/cells w/w | Cryoprotectant | TTR pH 5.5 (min) |
|---|---|---|---|---|
| *Streptococcus thermophilus* | | | | |
| C7 | Formate added to bacteria suspension prior to freezing | 0.4:1 | none | 458 |
| C8 | Frozen formate pellets added to frozen culture pellets | 0.4:1 | none | 282 |
| C9 | Formate added to bacteria suspension prior to freezing | 0.4:1 | Yes | 340 |
| C10 | Frozen formate pellets added to frozen culture pellets | 0.4:1 | Yes | 254 |
| *Lactobacillus bulgaricus* | | | | |
| C11 | Formate added to bacteria suspension prior to freezing | 0.4:1 | none | 640 |
| C12 | Frozen formate pellets added to frozen culture pellets | 0.4:1 | none | 578 |
| C13 | Formate added to bacteria suspension prior to freezing | 0.4:1 | Yes | 610 |
| C14 | Frozen formate pellets added to frozen culture pellets | 0.4:1 | Yes | 538 |
| C15 | Gistex added to bacteria suspension prior to freezing | 10:1 | none | 566 |
| C16 | Gistex added to frozen culture pellets | 10:1 | none | 482 |
| C17 | Gistex bacteria suspension prior to freezing | 10:1 | Yes | 502 |
| C18 | Gistex formate pellets added to frozen culture pellets | 10:1 | Yes | 458 |
| *Lactococcus lactis* | | | | |
| C19 | Formate added to bacteria suspension prior to freezing | 0.4:1 | none | 346 |
| C20 | Frozen formate pellets added to frozen culture pellets | 0.4:1 | none | 226 |
| C21 | Formate added to bacteria suspension prior to freezing | 0.4:1 | Yes | 266 |
| C22 | Frozen formate pellets added to frozen culture pellets | 0.4:1 | Yes | 216 |
| C23 | Maxarome added to bacteria suspension prior to freezing | 10:1 | none | 246 |
| C24 | Maxarome added to frozen culture pellets | 10:1 | none | 210 |
| C25 | Maxarome bacteria suspension prior to freezing | 10:1 | Yes | 236 |
| C26 | Maxarome formate pellets added to frozen culture pellets | 10:1 | Yes | 208 |

TABLE 4

Freeze dried culture compositions

| Composition | Stimulating additive (SA) | ratio SA/cells w/w | Cryo-protectant | TTR pH 5.5 (min) |
|---|---|---|---|---|
| *Streptococcus thermophilus* | | | | |
| C27 | Formate added to bacteria suspension prior to freezing | 0.4:1 | none | 442 |
| C28 | Formate powder added to the lyophilized culture | 0.4:1 | none | 346 |
| C29 | Formate added to bacteria suspension prior to freezing | 0.4:1 | Yes | 418 |
| C30 | Formate powder added to the lyophilized culture | 0.4:1 | Yes | 322 |
| C31 | Maxarome added to bacteria suspension prior to freezing | 10:1 | none | 334 |
| C32 | Maxarome added to the lyophilized culture | 10:1 | none | 328 |
| C33 | Maxarome added to bacteria suspension prior to freezing | 10:1 | Yes | 326 |
| C34 | Maxarome added to the lyophilized culture | 10:1 | Yes | 294 |
| *Lactobacillus bulgaricus* | | | | |
| C35 | Formate added to bacteria suspension prior to freezing | 0.4:1 | none | 718 |
| C36 | Formate powder added to the lyophilized culture | 0.4:1 | none | 526 |
| C37 | Formate added to bacteria suspension prior to freezing | 0.4:1 | Yes | 722 |
| C38 | Formate powder added to the lyophilized culture | 0.4:1 | Yes | 462 |
| *Lactococcus lactis* | | | | |
| C39 | Formate added to bacteria suspension prior to freezing | 0.4:1 | none | 398 |
| C40 | Formate powder added to the lyophilized culture | 0.4:1 | none | 348 |
| C41 | Formate added to bacteria suspension prior to freezing | 0.4:1 | Yes | 318 |
| C42 | Formate powder added to the lyophilized culture | 0.4:1 | Yes | 262 |
| C43 | Maxarome added to bacteria suspension prior to freezing | 10:1 | none | 370 |
| C44 | Maxarome added to the lyophilized culture | 10:1 | none | 270 |
| C45 | Maxarome added to bacteria suspension prior to freezing | 10:1 | Yes | 382 |
| C46 | Maxarome added to the lyophilized culture | 10:1 | Yes | 254 |

The invention claimed is:

1. A process for making a starter culture composition comprising a microorganism, a cryoprotectant and at least one stimulating additive, said process comprising:
   a. culturing a microorganism in a culture medium; and
   b. collecting the microorganism from the culture medium; and
   c. adding a cryoprotectant to the microorganism obtained in b); and
   d. freezing said microorganism obtained in c) in the form of pellets or granules; and
   e. adding at least one frozen stimulating additive in the form of pellets or granules to a microorganism obtained in d),
   wherein no stimulating additive is added before step d), and wherein said freezing of step d) is performed directly following the addition of cryoprotectant of step c);
   wherein the ratio of stimulating additive (wt.) to microorganism (wt.) in the starter culture composition is between 0.1 and 10; and
   wherein the addition of at least one frozen stimulating additive of step e) increases the acidification rate of the starter culture composition compared to addition of the stimulating additive before freezing, and
   wherein the cryoprotectant is added in an amount sufficient to increase the acidification rate of the starter culture composition compared to a composition without the added cryoprotectant.

2. The process according to claim 1, wherein said stimulating additive is a nutrient.

3. The process according to claim 1, wherein said stimulating additive is selected from the group consisting of a nucleobase, a yeast extract and formic acid and/or a salt and/or ester thereof.

4. The process according to claim 1, wherein the starter culture is a mixed culture.

5. The process according to claim 1, wherein said microorganism is a fungus or a bacterium.

6. The process according to claim 5, wherein the bacterium is a lactic acid bacterium.

7. The process according to claim 1, wherein said process further comprises packing the starter culture composition.

8. The process according to claim 1, wherein an additive selected from the group consisting of an excipient, a carrier and a nutrient is added to said microorganism before freezing.

9. A frozen starter culture composition comprising:
   a) frozen pellets or frozen granules comprising a microorganism and a cryoprotectant; and
   b) at least one frozen stimulating additive in the form of pellets or granules; wherein said at least one stimulating additive is selected from the group consisting of antioxidants, peptones, tryptones, vitamins, hydrolysates, amino acids, peptides, proteins, nucleic acids, nucleotides, nucleobases, yeast extracts, beef extract, organic acids, and growth factors;
   wherein no stimulating additive is present in the frozen pellets or granules comprising the microorganism and cryoprotectant,
   wherein the cryoprotectant is present in an amount effective for protection of the microorganism from damage during freezing and thawing and to increase the acidification rate of the starter culture composition, as compared to a composition without the cryoprotectant; and
   wherein the ratio of stimulating additive (wt.) to microorganism (wt.) in the starter culture composition is between 0.1 and 10; and
   wherein the at least one frozen stimulating additive increases the acidification rate of the starter culture composition as compared to a composition where a stimulating additive is frozen together with the microorganism and cryoprotectant.

10. A kit comprising at least a first packaging comprising the frozen pellets or frozen granules comprising a microorganism and a cryoprotectant according to claim 9 and a second packaging comprising the at least one frozen stimulating additive in the form of pellets or granules according to claim 9.

11. A process of producing a cultured food product, said process comprising:
   a. inoculating a precursor material with a frozen starter culture composition as defined in claim 9,
   b. culturing the precursor material with the frozen starter culture composition, and
   c. producing the cultured food product.

12. The process according to claim 11, wherein said cultured food product is selected from the group consisting of a dairy food product, a dairy food-derived product, a fermented milk product, a meat product, a vegetable product, a beverage product, a wine product, a bakery product, and a fruit juice product.

13. The process according to claim 11, wherein said precursor material is a dairy substrate.

14. The process according to claim 13, wherein said dairy substrate is milk.

\* \* \* \* \*